United States Patent [19]
Kuroda et al.

[11] 3,988,364
[45] Oct. 26, 1976

[54] NOVEL N,N-DI-SUBSTITUTED AMIDINES AND SEVERAL ACID-ADDITION SALTS THEREOF

[75] Inventors: Kiyoshi Kuroda, Shizuoka; Masyuki Hori, Shizuoka; Sadami Kobari, Mishima; Takeshi Shimizu, Shizuoka, all of Japan

[73] Assignee: Toyo Jozo Kabushiki Kaisha, Japan

[22] Filed: June 19, 1975

[21] Appl. No.: 588,184

Related U.S. Application Data

[63] Continuation of Ser. No. 422,136, Dec. 6, 1973, abandoned.

[30] Foreign Application Priority Data

Dec. 6, 1972 Japan.............................. 47-122773
Dec. 6, 1972 Japan.............................. 47-122774

[52] U.S. Cl...................... 260/501.14; 260/564 R; 424/316; 424/326
[51] Int. Cl.².................................. C07C 123/00
[58] Field of Search................... 260/564 R, 501.14

[56] References Cited
UNITED STATES PATENTS

| | | | |
|---|---|---|---|
| 3,598,800 | 8/1971 | Gätzi.............................. | 260/564 R |
| 3,689,675 | 9/1972 | Knowles......................... | 260/564 R |
| 3,786,094 | 1/1974 | Perronnet et al.............. | 260/564 R |

*Primary Examiner*—Gerald A. Schwartz
*Attorney, Agent, or Firm*—Holman & Stern

[57] ABSTRACT

The invention relates to a group of novel N,N'-di-substituted amines, especially adapted for use as antitussive agent.

These compounds can be expressed by the following general formula:

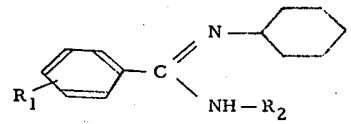

wherein
$R_1$ stands for a member selected from the group consisting of hydrogen, methyl and methoxy;
$R_2$ stands for a member selected from the group consisting of phenyl, tolyl, xylyl, ethylphenyl, o- and m-methoxyphenyl, trimethylphenyl and α-naphthyl.

40 Claims, No Drawings

NOVEL N,N-DI-SUBSTITUTED AMIDINES AND SEVERAL ACID-ADDITION SALTS THEREOF

This is a continuation of application Ser. No. 422,136 filed Dec. 6, 1973 now abandoned.

This invention relates to novel N,N'-di-substituted amidines and several acid-addition salts thereof.

These novel amidines are expressed by the following general formula (I).

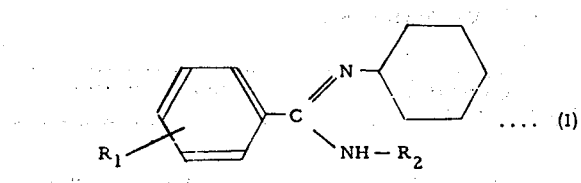 .... (I)

wherein
$R_1$ stands for a member selected from the group consisting of hydrogen, methyl and methoxy; and
$R_2$ stands for a member selected from the group consisting of tolyl, xylyl, ethylphenyl, methoxyphenyl, trimethylphenyl and α-naphtyl.

These novel amidines and their pharmacologically allowable acid addition salts are, according to our experimental results, highly effective as antitussive agent.

As the antitussive agents, picoperidamine hydrochloride, carbetapentane citrate, "Hustazol", dextromethorphan hydrobromide, noscapine hydrochloride, codeine phosphate and the like are very commonly known and find nowadays their broad clinical use. However, other conventional antitussive agents than codeine phosphate are known to have rather weak antitussive effect, while codeine phosphate has a strong effect in the above sense, but those persons administered therewith are suffered from appreciable habituation which fact inhits a long extended continuous administration thereof.

It is a main object of the present invention to provide a group of novel compounds expressed by the foregoing general formula and several acid addition salt derivatives therefrom, being highly effective when used in antitussive purposes.

A further object is to provide a process for the manufacture of the said novel compounds.

In the course of our profound screening experiments for obtaining more efficient antitussive agents, we have found that novel N,N'-di-substituted amidines having the aforementioned general formula (I) show a remarkable such effect.

In our experiments using dogs for administration, it has been found that the said novel compounds have a powerful antitussive effect comparable with that of codeine phosphate, while they represent rather weak acute toxicity and substantially no respiratory-depressing, analgesic and constipating effects and thus, are pharmacologically highly valuable.

We have further found that the novel amidine-(I) according to the foregoing general formula (I) represents the following tautomerism:

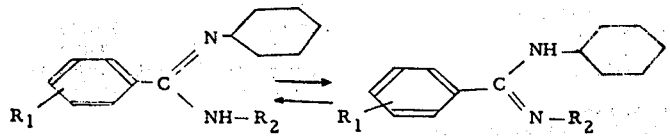

wherein
$R_1$ and $R_2$ have respective same meanings as before.
Therefore, this tautomeric isomer is within the gist and scope of the invention.

In order to prepare the amidine-(I), imino-compound which may be expressed by the following general formula (II):

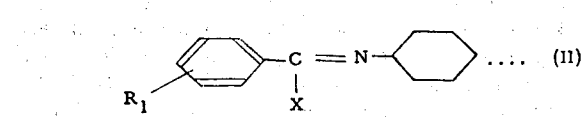 .... (II)

wherein
X stands for halogen or YR' radical;
R' stands for lower alkyl or aralkyl;
Y stands for O or S;
$R_1$ has the same meaning as before;
is reacted with amine having the following general formula (III):

wherein
$R_2$ has the same meaning as before.

The novel compound, amidine-(I) shows, as aforementioned, the tautomerism thus, a replacement of the cyclohexyl radical of the above imino-compound, to be denoted the imino-compound-(III) hereinafter, by $R_2$-radical of the above-mentioned amine, to be called the amine-(III), will lead through the similar reaction to the same amidine-(I).

The imino-compound-(II) carries a radical capable of reacting with amino radical, such as halogen, OR'- or SR-radical, the meaning of R' being same as before, and can be prepared in the known way. As an example, imino halide which corresponds to such compound wherein in the general formula (II) X stands for halogen, can be prepared by reaction of the corresponding N-substituted amide, such as N-cyclohexyl-o-toluamide, N-phenyl-m-toluamide, N-m-tolyl-m-toluamide, N-cyclohexyl-benzamide, N-o-tolyl-benzamide, N-2,3-xylylbenzamide, N-α-naphtyl-benzamide or the like, with a halogenation agent, such as $PCl_5$, $PCl_3$, $POCl_3$, $COCl_2$, $SOCl_2$, benzene sulfonic acid chloride, p-toluene sulfonic acid chloride or the like, of which $COCl_2$ is highly preferable. In a representative manufacturing process, N-substituted amide is dissolved in a dehydrated inert organic solvent, such as tetrahydrofuran, benzene, dioxane, toluene, chloroform, dichloromethane or the like, and gaseous or liquid state $COCl_2$ is introduced directly into the solution for reaction and in the presence of tertiary amine, such as triethylamine, dimethylaniline, pyridine or the like. Or alternatively, $COCl_2$ may be used in the form of a solution in benzene, toluene or the like. Then, the tertiary amine hydrochloride is removed and the thus obtained mother liquor is condensed even at a low temperature to provide imino chloride. The imino chloride can be exclusively extracted from the condensate by use of an inert organic solvent, not dissolving N-substituted amide, such as, for instance, petroleum ether, n-hexane, cyclohexane or the like.

Imino (thio) ether which corresponds when X is YR' can be prepared in such way that imino halide is reacted under anhydrous conditions with (thio) alcohol or sodium (thio) alcolate. The above R'-radical may specifically be methyl, propyl, butyl or the like lower alkyl, or benzyl or the like aralkyl and Y is O or S, as the case may be.

The amine-(III) usable in the present invention may be cyclohexyl amine or aromatic amine which may be expressed by the general formula: $R_2 - NH_2$. As an example, o-, m- or p-toluidine, p-ethylaniline, 3,4-xylidine, o-, m- or p-anisidine, α-naphtyl amine or the like may be raised.

When the amine-(III) is cyclohexyl amine, the cyclohexyl of the imino-compound-(II) corresponds to said radical $R_2$.

The reaction of the imino-compound (II) with the amine-(III) can be brought about in the presence of an inert organic solvent capable of dissolving the imino-compound (II), such as, for instance, petroleum ether, n-hexane, cyclohexane, benzene, tetrahydrofuran, dioxane, chloroform or the like. The reaction progress normally under lower temperature or room temperature. Should the reaction progress only at a low speed, the reaction system can be warmed up.

The formed amidine-(I) can be obtained by condensation of the reaction liquid. Or alternatively, the sedimented products are separated out and dissolved in aqueous acidic solution, as an example by use of diluted hydrochloric acid. Then, the thus obtained aqueous solution is washed with a hydrophobic organic solvent, such as ethyl acetate, butyl acetate, chloroform, dichloromethane or the like and the amidine-(I) is obtained as deposits and in the form of a salt of an acid such as hydrochloric acid. Or alternatively, by addition of alkali, the thus isolated basic compound can be extracted with water immiscible organic solvent.

The thus isolated basic compound may be reacted with an inorganic acid, such as hydrochloric acid, or suitable organic acid, so as to form a corresponding acid addition salt.

The antitussive activity and acute toxicity of the group of the novel compounds according to this invention are as follows:

1. Antitussive activity:

| route of administration: | intravenous injection; |
|---|---|
| antitussive activity: | |

From the efficiency rate obtained upon each administration step, 50%-antitussive effective dose ($AtD_{50}$) was calculated according to the Litchfield-Wilcoxon method. Further, efficiency ratio relative to codeine phosphate was also determined.

2. Acute Toxicity:

| test animals: | more than five groups, each group consisting of five male mice of ddy-strain |
|---|---|
| route of administration: | subctaneous injection; |
| acute toxicity: | |

From the mortality as determined after 72 hours of each administration step, 50%-lethal dose ($LD_{50}$) was calculated by the Litchfield-Wilcoxon method.

3. Results:

The results were as follows.

| | Compound | Antitussive Ratio | $LD_{50}$ (mg./kg.) |
|---|---|---|---|
| 1. | hydrochloric acid salt of N-cyclohexyl, N'-o-tolyl-benzamidine | 1.73 | 242 |
| 2. | hydrochloric acid salt of N-cyclohexyl, N'-p-tolyl-benzamidine | 0.58 | 186 |
| 3. | hydrochloric acid salt of N-cyclohexyl, N'-p-ethylphenyl | 0.95 | 218.5 |
| 4. | hydrochloric acid salt of N-cyclohexyl, N'-2,3-xylyl-benzamidine | 1.21 | 117 |
| 5. | hydrochloric acid salt of N-cyclohexyl, N'-o-methoxyphenyl | 0.44 | 268 |
| 6. | hydrochloric acid salt of N-cyclohexyl, N'-m-methoxyphenyl | 1.20 | 78 |
| 7. | hydrochloric acid salt of N-cyclohexyl, N'-α-naphthyl | 0.79 | >800 |
| 8. | hydrochloric acid salt of N-cyclohexyl, N'-phenyl-m-toluamidine | 1.20 | 276 |
| 9. | hydrochloric acid salt of N-cyclohexyl, N'-m-tolyl-m-toluamidine | 1.20 | 445 |
| 10. | hydrochloric acid salt of N-cyclohexyl, N'-phenyl-p-toluamidine | 0.83 | 186 |
| 11. | picoperidamine hydrochloride | 0.95 | 144 |
| 12. | carbetapentane citrate | 0.26 | 186.5 |
| 13. | Hustazol | 0.52 | 375 |
| 15. | dextrometrofan hydrobromide | 0.15 | 153 |
| 16. | noscapine hydrochloride | 0.24 | 240 |
| 17. | codeine phosphate | 1.00 | 190 |
| 18. | N-cyclohexyl, N'-phenol-o-toluamidine hydrochloride | $AtD_{50}$ (mg./kg.) 5.15 | $LD_{50}$ (mg./kg.) 740 |
| 19. | N-cyclohexyl, N'-o-tolyl-o-toluamidine | | |

-continued

| | Compound | Antitussive Ratio | LD$_{50}$ (mg./kg.) |
|---|---|---|---|
| | hydrochloride | 5.15 | 650 |
| 20. | N-cyclohexyl, N'-m-tolyl-o-toluamidine hydrochloride | 4.29 | >100 |
| 21. | N-cyclohexyl, N'-p-tolyl-o-toluamidine hydrochloride | 3.58 | 160 |
| 22. | N-cyclohexyl, N'-2,3,-xylyl-o-toluamidine hydrochloride | 3.58 | >1000 |
| 23. | N-cyclohexyl, N'-o-methoxyphenyl-m-toluamidine hydrochloride | 4.29 | 100 |
| 24. | N-cyclohexyl, N'-m-methoxyphenyl-o-toluamidine oxalate | 5.15 | 891 |
| 25. | N-cyclohexyl, N'-p-tolyl-m-toluamidine hydrochloride | 4.29 | 900 |
| 26. | N-cyclohexyl, N'-o-tolyl-m-toluamidine hydrochloride | 2.98 | 740 |
| 27. | N-cyclohexyl, N'-o-ethylphenyl-m-toluamidine hydrochloride | 5.15 | >1000 |
| 28. | N-cyclohexyl, N'-m-methoxyphenyl-m-toluamidine oxalate | 5.15 | 743 |
| 29. | N-cyclohexyl, N'-o-tolyl-p-toluamidine hydrochloride | 2.48 | 620 |
| 30. | N-cyclohexyl, N'-o-ethylphenyl-p-toluamidine hydrochloride | 4.29 | >1000 |
| 31. | N-cyclohexyl, N'-2,3,-xylyl-p-toluamidine hydrochloride | 2.07 | >1000 |
| 32. | N-cyclohexyl, N'-m-tolyl-p-toluamidine hydrochloride | 2.48 | 460 |
| 33. | N-cyclohexyl, N'-m-methoxyphenyl-p-toluamidine hydrochloride | 5.15 | 600 |
| 34. | N-cyclohexyl, N'-phenyl-o-methoxy-benzamidine hydrochloride | 3.58 | 100 |
| 35. | N-cyclohexyl, N'-m-tolyl-o-methoxy-benzamidine hydrochloride | 5.15 | 144 |
| 36. | N-cyclohexyl, N'-o-tolyl-o-methoxy-benzamidine hydrochloride | 4.29 | 100 |
| 37. | N-cyclohexyl, N'-m-methoxyphenyl-o-methoxybenzamidine hydrochloride | 2.98 | 207 |
| 38. | N-cyclohexyl, N'-phenyl-p-anisamidine hydrochloride | 2.98 | 120 |
| 39. | N-cyclohexyl, N'-o-tolyl-p-anisamidine hydrochloride | 3.58 | 172 |
| 40. | N-cyclohexyl, N'-m-tolyl-p-anisamidine hydrochloride | 2.48 | 298 |
| 41. | N-cyclohexyl, N'-m-methoxyphenyl-p-anisamidine hydrochloride | 2.98 | 248 |
| 42. | N-cyclohexyl, N'-o-ethylphenyl-benzamidine hydrochloride | 4.29 | >1000 |
| 43. | N-cyclohexyl, N'-3,5-xylyl-benzamidine hydrochloride | 3.58 | 660 |
| 44. | N-cyclohexyl, N'-m-ethylphenyl-benzamidine hydrochloride | 4.29 | 900 |
| 45. | N-cyclohexyl, N'-2,6-xylyl-benzamidine hydrochloride | 4.29 | 248 |
| 46. | N-cyclohexyl, N'-2,4,6-trimethyl-phenyl-benzamidine hydrochloride | 5.15 | 120 |
| 47. | codeine phosphate | 2.2 | 190 |

In the following several manufacturing numerical examples will be given for better understanding of the invention.

EXAMPLE 1

Preparation of N-cyclohexyl, N'-phenyl-m-toluamidine 65.1 g (0.3 mole) of N-cyclohexyl-m-toluamide were dissolved in 500 ml of dried tetrahydrofuran and a benzene solution of 45 g of $COCl_2$ absorbed in 30 ml dried benzene, and 30 ml dried pyridine were added dropwise and under agitation and ice cooling to the above tetrahydrofuran solution. Upon completion of the dropwise addition, the reaction mixture was adjusted in its temperature to room temperature and brought into reaction for 2 hours. The sedimented pyridine hydrochloride were filtered off and the filtrate was condensed under vacuo, to provide an oily substance containing N-cyclohexyl-m-toluimido chloride. The oil was then subjected to extraction with 400 ml of dried petroleum ether and 32.8 ml (0.36 mole) of aniline were added dropwise for 30 minutes under agitation and ice cooling to the extract and the mixture was let to react at room temperature for 1.5 hours. The thus deposited oily substance was decanted off from the mother liquor and dissolved in 100 ml of ethanol, adjusted pH to about 2 by addition of 1N-hydrochloric acid and added with 1.2 lit. of water. Then, the aqueous solution was washed twice with 150 ml of ethyl acetate. The aqueous phase was treated with active carbon for discoloration and then condensed under vacuo. The sedimented products were filtered off, washed, dried and recrystallized from ethanol/diethyl ether. In this way, 81.7 g of N-cyclohexyl, N'-phenyl-m-toluamidine were obtained. m.p. 174° – 176° C. Yield: 82.9%.

| | Based upon $C_{20}H_{25}N_2Cl$, | | |
|---|---|---|---|
| | C, % | H, % | N, % |
| calct'd | 73.04 | 7.66 | 8.52 |
| found | 72.97 | 7.82 | 8.82 |

EXAMPLE 2

Preparation of N-cyclohexyl, N'-m-tolyl-m-toluamidine hydrochloride

In Example 1, 390 ml of m-toluidine were used in place of 32.8 ml of aniline. In this way, 77.7 g of N-cyclohexyl, N'-m-tolyl-m-toluamidine hydrochloride were obtained. m.p. 149° – 151° C. Yield: 75.7%.

| | Based upon $C_{21}H_{27}N_2Cl$, | | |
|---|---|---|---|
| | C, % | H, % | N, % |
| calcul't | 73.56 | 7.94 | 8.17 |
| found: | 73.72 | 7.90 | 8.44 |

EXAMPLE 3

Preparation of N-cyclohexyl, N'-phenyl-p-toluamidine chloride 86.8 g (0.4 mole) of N-cyclohexyl-p-toluamide were dissolved in 600 ml of dried tetrahydrofuran and added dropwise with a solution of 60 g (0.6 mole) of $COCl_2$ in dried benzene and 40 ml of dried pyridine, under agitation and ice cooling.

Upon completion of the dropwise addition, the mixture was adjusted in its temperature to room temperature and held stationary for reaction for about 2 hours. The sedimented pyridine hydrochloride was filtered off and the mother liquor was condensed under vacuo to provide an oily substance containing N-cyclohexyl-p-toluimidochloride which was then subjected to extraction with 500 ml of dried petroleum ether. The extract was added dropwise with 43.7 ml (0.48 mole), under agitation and ice cooling, for 30 minutes and kept stationary for 1.5 hours at room temperature for reaction. The sedimented phase was added with 150 ml of ethanol and the pH was adjusted to about 2. And the mixture was added with 1 lit. of water and the aqueous solution was washed twice with 200 ml of ethyl acetate.

Then, the aqueous phase was treated with active carbon for discoloration and condensed under vacuo. The sedimented phase was filtered off, washed, dried and finally recrystallized from ethanol/diethyl ether. In this way, 101 g of N-cyclohexyl, N'-phenyl-p-toluamidine hydrochloride were obtained. m.p.: 211° – 213° C. Yield: 76.8%.

| | Based upon $C_{20}H_{25}N_2Cl$, | | |
|---|---|---|---|
| | C, % | H, % | N, % |
| calcul'd: | 73.04 | 7.66 | 8.52 |
| found: | 72.88 | 7.81 | 8.30 |

EXAMPLE 4

Preparation of N-cyclohexyl, N'-m-tolyl-m-toluamidine 90.1 g (0.4 mole) of N-m-tolyl-m-toluamide were dissolved in 600 ml of dried tetrahydrofuran and added dropwise with a solution of 60 g (0.8 mole) of $COCl_2$ in 40 ml of dried benzene, and with 40 ml of dried pyridine, under agitation and ice cooling. After completion of said dropwise addition, the mixture was adjusted in its temperature to room temperature and kept stationary for about 2 hours for reaction. The sedimented pyridine hydrochloride was filtered off, while the filtrate was condensed to provide an oily substance containing N-m-tolyl-m-toluimidochloride. The oily phase was subjected to extraction with 500 ml of dried petroleum ether and the extract was added dropwise with 54.1 ml (0.48 mole) of cyclohexyl amine under agitation and ice cooling for 30 minutes and kept stationary for reaction at room temperature for an hour. The thus sedimented oily substance was separated by decantation from the mother liquor and dissolved with 150 ml of ethanol, and the pH was adjusted to about 2 by addition of 1N-hydrochloric acid. Then, the mixture was added with 1.2 lit. of water and the aqueous solution was washed twice with 150 ml of ethyl acetate. The aqueous phase was treated with active carbon for discoloration and condensed under vacuo. The sedimented products were filtered off, washed, dried and recrystallized from ethanol/diethyl ether. The thus obtained N-cyclohexyl, N'-m-tolyl-m-toluamidine chloride were obtained. Yield: 72.8% (100 g). m.p.: 149° – 151° C.

EXAMPLE 5

Preparation of N-cyclohexyl, N'-o-tolyl-benzamidine hydrochloride

N-cyclohexyl-benzamidine, 81.2 g (0.4 mole) was dissolved in dried tetrahydrofuran, 600 ml, and added dropwise with a solution of $COCl_2$, 60 g (0.6 mole) in dried benzene, 40 ml, and with dried pyridine, 40 ml, under agitation and ice cooling. Upon completion of this dropwise addition, the mixture was adjusted in its temperature to room temperature and kept stationary for reaction for about 2 hours. The sedimented pyridine hydrochloride was filtered off, while the filtrate was condensed under vacuo, to provide an oily substance containing N-cyclohexyl-benzimidochloride. The oil phase was extracted with 500 ml of dried petroleum ether, and the extract was added dropwise for 30 minutes with 51 g (0.48 mole) of o-toluidine, under agitation and ice cooling, and kept stationary at room temperature for 1.5 hours. The produced oil phase was decanted for separation from the mother liquor and dissolved with 100 ml of ethanol. The pH was adjusted to about 2 by addition of 1N-hydrochloric acid and added further with about 1 lit. of water. Then, the aqueous solution was washed twice with 150 ml of ethyl acetate, treated with active carbon for discoloration and condensed under vacuo. The sedimented products were filtered off, washed, dried and recrystallized from ethanol/diethyl ether. In this way, N-cyclohexyl, N'-o-tolyl-benzamidine hydrochloride. m.p.: 208° – 211° C. Yield: 106.4 g (81%).

|          | Based upon $C_{20}H_{25}N_2Cl$, | | |
|----------|------|------|------|
|          | C, % | H, % | N, % |
| calcul'd: | 73.04 | 7.66 | 8.52 |
| found:    | 72.73 | 7.63 | 8.52 |

EXAMPLE 6

In place of o-toluidine (0.48 mole) in Example 5, p-ethyl aniline; 2,3-xylidine; o-anisidine; m-anisidine; α-naphtylamine and p-toluidine were used, respectively, and the following compounds were produced, respectively.

N-cyclohexyl, N'-p-ethylphenyl-benzamidine hydrochloride; m.p.: 182° – 183° C. Yield: 77.3%.
N-cyclohexyl, N'-3,4-xylyl-benzamidine hydrochloride; m.p.: 213° –215° C, Yield: 72.4%.
N-cyclohexyl, N'-o-methoxyphenyl-benzamidine hydrochloride; 194° – 196° C, Yield: 81.3%.
N-cyclohexyl, N'-m-methoxyphenyl-benzamidine hydrochloride; m.p.: 140° – 142° C, Yield: 76.4%.
N-cyclohexyl, N'-α-naphtyl-benzamidine hydrochloride, m.p.: 254° – 255° C. Yield: 82.7%, and
N-cyclohexyl, N'-p-tolyl-benzamidine hydrochloride; m.p.: 202° – 204° C, Yield: 82.1%, respectively.

The embodiments of the invention in which an exclusive property or privilege is claimed are as follows:

1. N,N'-di-substituted amidine having the following general formula:

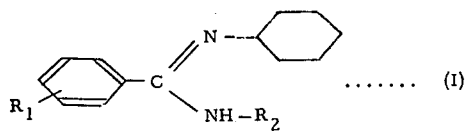

(I)

wherein
R₁ stands for a member selected from the group consisting of hydrogen, methyl and methoxy;
R₂ stands for a member selected from the group consisting of phenyl; tolyl, xylyl, ethylphenyl, o- and m-methoxyphenyl; and trimethylphenyl.

2. Pharmacologically allowable acid addition salt of the compound according to claim 1.
3. N-cyclohexyl, N'-o-tolyl-benzamidine hydrochloride.
4. N-cyclohexyl, N'-p-tolyl benzamidine hydrochloride.
5. N-cyclohexyl, N'-p-ethylphenyl-benzamidine hydrochloride.
6. N-cyclohexyl, N'-2,3-xylyl-benzamidine hydrochloride.
7. N-cyclohexyl, N'-o-methoxyphenyl-benzamidine hydrochloride.
8. N-cyclohexyl, N'-m-methoxyphenyl-benzamidine hydrochloride.
9. N-cyclohexyl, N'-phenyl-m-toluamidine hydrochloride.
10. N-cyclohexyl, N'-m-tolyl-m-toluamidine hydrochloride.
11. N-cyclohexyl, N'-phenyl-p-toluamidine hydrochloride.
12. N-cyclohexyl, N'-phenyl-o-toluamidine hydrochloride.
13. N-cyclohexyl, N'-o-tolyl-o-toluamidine hydrochloride.
14. N-cyclohexyl, N'-m-tolyl-o-toluamidine hydrochloride.
15. N-cyclohexyl, N'-p-tolyl-o-toluamidine hydrochloride.
16. N-cyclohexyl, N'-2,3-xylyl-o-toluamidine hydrochloride.
17. N-cyclohexyl, N'-o-methoxyphenyl-m-toluamidine hydrochloride.
18. N-cyclohexyl, N'-m-methoxyphenyl-o-toluamidine oxalate.
19. N-cyclohexyl, N'-p-tolyl-m-toluamidine hydrochloride.
20. N-cyclohexyl, N'-o-tolyl-m-toluamidine hydrochloride.
21. N-cyclohexyl, N'-o-ethylphenyl-m-toluamidine hydrochloride.
22. N-cyclohexyl, N'-m-methoxyphenyl-m-toluamidine oxalate.
23. N-cyclohexyl, N'-o-tolyl-p-toluamidine hydrochloride.
24. N-cyclohexyl, N'-o-ethylphenyl-p-toluamidine hydrochloride.
25. N-cyclohexyl, N'-2,3-xylyl-p-toluamidine hydrochloride.
26. N-cyclohexyl, N'-m-tolyl-p-toluamidine hydrochloride.
27. N-cyclohexyl, N'-m-methoxyphenyl-p-toluamidine hydrochloride.
28. N-cyclohexyl, N'-phenyl-o-methoxybenzamidine hydrochloride.
29. N-cyclohexyl, N'-m-tolyl-o-methoxy-benzamidine hydrochloride.
30. N-cyclohexyl, N'-o-tolyl-o-methoxy-benzamidine hydrochloride.
31. N-cyclohexyl, N'-m-methoxyphenyl-o-methoxybenzamidine hydrochloride.
32. N-cyclohexyl, N'-phenyl-p-anisamidine hydrochloride.
33. N-cyclohexyl, N'-o-tolyl-p-anisamidine hydrochloride.
34. N-cyclohexyl, N'-m-tolyl-p-anisamidine hydrochloride.
35. N-cyclohexyl, N'-m-methoxyphenyl-p-anisamidine hydrochloride.

36. N-cyclohexyl, N'-o-ethylphenyl-benzamidine hydrochloride.

37. N-cyclohexyl, N'-3,5-xylyl-benzamidine hydrochloride.

38. N-cyclohexyl, N'-m-ethylphenyl-benzamidine hydrochloride.

39. N-cyclohexyl, N'-2,6-xylyl-benzamidine hydrochloride.

40. N-cyclohexyl, N'-2,4,6-trimethylphenyl-benzamidine hydrochloride.

* * * * *